United States Patent
Gerlach et al.

(10) Patent No.: US 7,854,159 B2
(45) Date of Patent: Dec. 21, 2010

(54) SENSOR AND METHODS FOR MEASURING OF CONCENTRATIONS OF COMPONENTS IN A LIQUID

(75) Inventors: Gerald Gerlach, Dresden (DE); Jörg Sorber, Schönteichen (DE); Margarita Günther, Dresden (DE)

(73) Assignee: Technische Universität Dresden, Dresden (DE)

( * ) Notice: Subject to any disclaimer, the term of this patent is extended or adjusted under 35 U.S.C. 154(b) by 504 days.

(21) Appl. No.: 11/811,072

(22) Filed: Jun. 8, 2007

(65) Prior Publication Data
US 2007/0295061 A1    Dec. 27, 2007

(30) Foreign Application Priority Data
Jun. 8, 2006    (DE) .................. 10 2006 026 668

(51) Int. Cl.
*G01N 33/00* (2006.01)
*G01N 33/487* (2006.01)
(52) U.S. Cl. .................. 73/61.41; 435/287.1; 600/345; 600/347
(58) Field of Classification Search ............. 435/287.1; 73/61.41, 61.47, 61.48; 600/345, 346, 347, 600/348, 362, 363, 364, 365, 366
See application file for complete search history.

(56) References Cited

U.S. PATENT DOCUMENTS

| | | | | |
|---|---|---|---|---|
| 3,870,065 A | * | 3/1975 | Minns, Jr. ...................... | 137/93 |
| 4,361,026 A | * | 11/1982 | Muller et al. .............. | 73/24.01 |
| 4,631,952 A | | 12/1986 | Donaghey | |
| 4,637,101 A | * | 1/1987 | Fiedler ......................... | 24/602 |
| 4,813,424 A | | 3/1989 | Wilkins | |
| 5,120,505 A | | 6/1992 | Lowell, Jr. et al. | |
| 5,141,873 A | * | 8/1992 | Steudle et al. .............. | 436/148 |
| 5,514,338 A | | 5/1996 | Simon et al. | |
| 5,563,341 A | | 10/1996 | Fenner | |
| 6,201,980 B1 | * | 3/2001 | Darrow et al. .............. | 600/347 |
| 6,264,612 B1 | * | 7/2001 | McConnell et al. ......... | 600/486 |
| 6,315,956 B1 | | 11/2001 | Foulger | |

(Continued)

FOREIGN PATENT DOCUMENTS

EP    0539625    5/1993

(Continued)

*Primary Examiner*—Lisa M Caputo
*Assistant Examiner*—Punam Roy
(74) *Attorney, Agent, or Firm*—Horst M. Kasper

(57) ABSTRACT

A sensor for measuring the concentration of components in a liquid, exhibiting a base body with a deformation body, and a hollow chamber. The hollow chamber is on the one side deformable through the deformation body and on the other side rigidly closed. The hollow chamber is completely filled with a swellable polymeric network, which network exhibits a volume phase transition at a certain concentration of components in the liquid. The liquid can have contact to the polymeric network through at least one opening in at least one of the rigid delimiting sides of the hollow chamber. A mechano electrical transducer detects the deflection of the deformation body. The sensor exhibits a servo device (8) working on the deformation body (3), wherein the servo device (8) can be controlled through a control member with a comparator unit (9) such that the deflection of the deformation body (3) is compensated, wherein the corresponding control signal for the servo device (8) represents the measurement value for the concentration of components in the liquid (1).

19 Claims, 2 Drawing Sheets

U.S. PATENT DOCUMENTS

Figure 1:
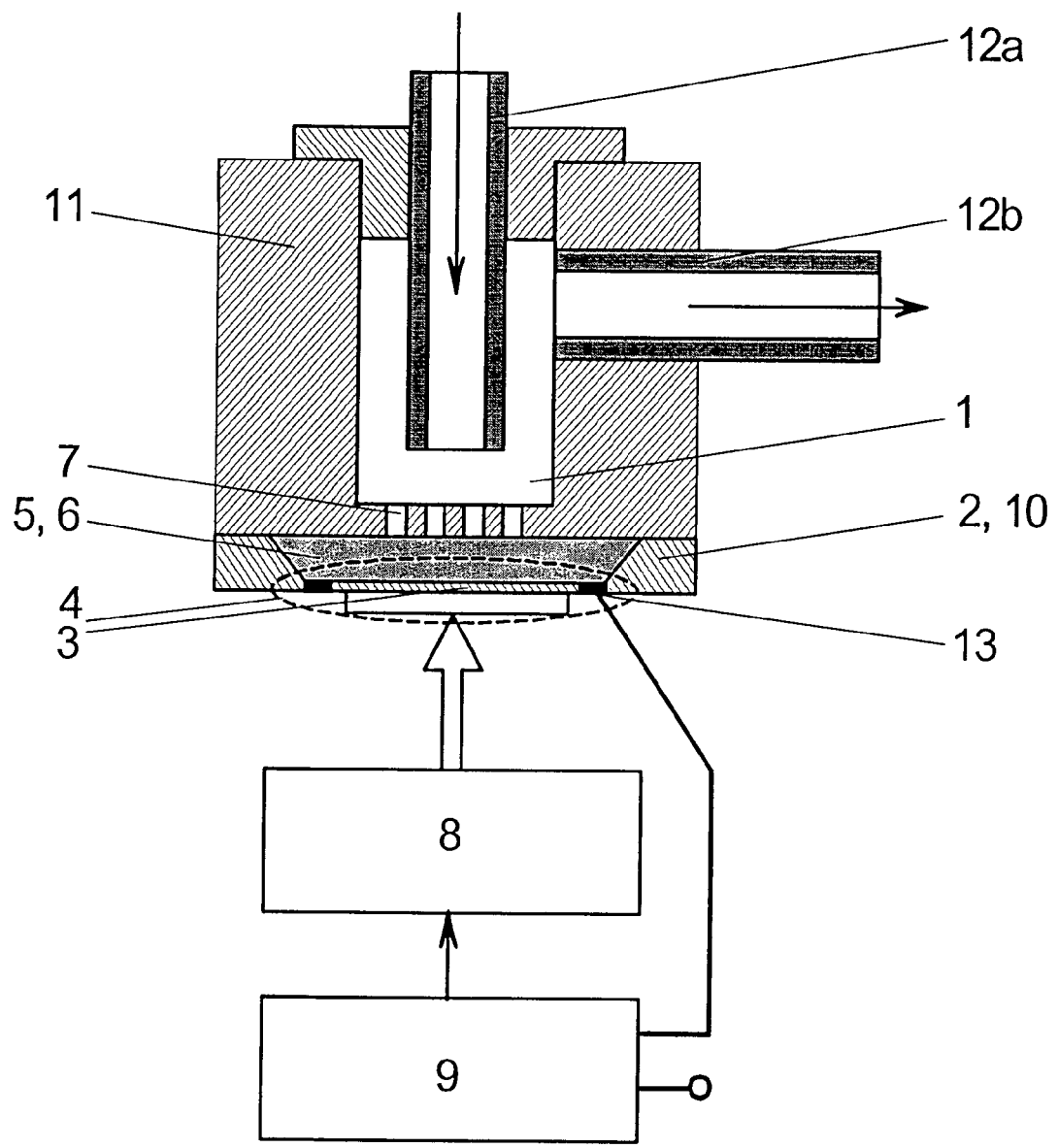

| | | |
|---|---|---|
| 6,475,750 B1 | 11/2002 | Han et al. |
| 6,514,689 B2 | 2/2003 | Han et al. |
| 6,753,191 B2 | 6/2004 | Asher et al. |
| 6,835,553 B2 * | 12/2004 | Han et al. ............ 435/14 |
| 2001/0016683 A1 * | 8/2001 | Darrow et al. ......... 600/347 |
| 2005/0003517 A1 | 1/2005 | Ragless |
| 2006/0078984 A1 | 4/2006 | Moyle et al. |

FOREIGN PATENT DOCUMENTS

| | | |
|---|---|---|
| EP | 1467198 | 10/2004 |
| WO | 0010007 | 2/2000 |
| WO | 0233732 | 4/2002 |
| WO | 2004/064623 | 8/2004 |
| WO | 2006/011062 | 2/2006 |

* cited by examiner

SENSOR AND METHODS FOR MEASURING OF CONCENTRATIONS OF COMPONENTS IN A LIQUID

FIELD OF THE INVENTION

The Invention relates to a sensor and a method for measuring the concentration of chemical components in liquids. For this purpose the capability of swelling of suitable polymer networks relative to one component or several component liquids shall be utilized in particular for a solid-state sensor on a semiconductor basis.

STATE-OF-THE-ART

It is known that certain polymer networks in liquids exhibit a volume phase transition with a strong change in volume depending on the concentration and the kind of the certain components (S. H. Gehrke: synthesis, equilibrium swelling, genetics, permeability and applications of environmentally responsive gels, Adv. Polym. Sci. 110 (1993), 81-144). This property of the so-called smart polymer networks renders them useful for the sensing of liquids. A measurement signal capable of coordination is obtainable based on the fact that for each state of the liquid there exists exactly one swelling state of the polymer network and that this effect is reversible. Polymer networks without the volume phase transition behavior can only conditionally again de-swell and are less suitable for the application as measurement value receiver based on the substantially limited reversibility of the effect.

Sensitive polymer networks as measurement value receiver for the sensing of liquids or, respectively, suitable transducer principles are known from the following literature documents:

The mass of the layer changes based on the reception of particles in the polymer layer and therewith the resonance frequency of an oscillating structure, where the layer is part of the oscillating a structure (German printed Patent document DE 19848878 A1; A Schroth, K. Sager, G. Gerlach, H. Haberli, T. Boltshauser, H. Baltes: A resonant polyimide-based humidity sensor. Sensors and Actuators B, 34 (1996), 301). The change of the resonance frequency then forms the electrical output signal.

The mass change of a polymer layer based on particle reception can also be transformed into an electrical output signal, if the polymer layer is part of a delay line or part of a resonance body, where in particular the wave propagation at the surface of a solid body or the frequency change is influenced by the changeable mass coating of the layer disposed thereupon (German printed Patent document DE 19848878 A1) This measurement principle has the limited miniaturerizability of the sensor as an essential disadvantage. AT-oscillator quartz pieces have for example a diameter of from 10 to 20 mm.

The polymer networks with a volume phase transition, which are also designated as smart polymer networks, are known from the following literature documents:

Hydro gels out of polyvinyl alcohol/polyacrylic acid show a pH-sensitive volume phase transition (K.-F. Arndt, A. Richter, S. Ludwig, J. Zimmermann, J. Kressler, D. Kuckling, H.-J. Adler: Poly(vinyl alcohol)/poly(acrylic acid) hydro gels: FT-IR spectroscopic characterization and work at transition point. Acta Polymerica 50 (1999), 383-390).

Copolymers of the N-iso-propyl-acryl-amide with comonomers, which contain acid groups or basic groups, show a temperature dependent volume phase transition, wherein the temperature of the volume phase transition can be adjusted through the pH-value of the swelling agent (D. Kuckling, H.-J. Adler, K.-F. Arndt, L. Ling, W.-D. Habicher: Temperature and pH-depending solubility of novel PNIPAAm-copolymers. Makromol. Chem. Phys. 201 (2000), 273-280).

The phase transition temperature in aqueous solvent mixtures changes for poly acryl amide depending on the concentration and the kind of the added component (H.-G. Schild, M. Muthukumar, D.-A. Tirrell: Co-non-solvency in mixed aqueous solutions of poly(N-isopropylacrylamide). Macro-molecules 24 (1991), 948-952). The polymer networks therefore show a swelling depending on the concentration and the kind of the organic solvent component at constant temperature.

Polymers capable of swelling (organo gels) also in organic solvents can exhibit volume phase transitions, as has been shown by way of example with a poly-di-methyl-siloxane network in a mixed solution agent (L. Rogovina, V. Vasiliev, G. Slonimsky: Influence of the thermodynamical quality of the solvent on the properties of poly di-methyl siloxane networks in swollen and dry state. Progr. Colloid & Polymer Sci. 90 (1992), 151-155).

It is now proposed in German printed Patent document 19828093 to employ sensitive polymer networks as measurement value receivers, in order to measure pH values, ionic concentrations and material concentrations or contents of dissolved, non-dissolved or dispersed organic or inorganic materials.

According to one of the proposed forms of the measurement value receiver, the swelling behavior is evaluated as a sensing effect, wherein the polymer network is performed as a freestanding, against a spring working, large volume material or as a planar support material, which carries an extension measurement strip. The two solutions exhibit decisive disadvantages. The two solutions cannot be miniaturerized in this form and the liquid with the components to measure operates according to the two solutions directly onto the electrical sensor components.

In German Democratic Republic Patent document DD 236173, in German printed Patent document DE 4312788 C2, in German printed Patent document DE 19842514 C1, and in U.S. Pat. No. 5,563,341 solutions are presented for bimorphous humidity and gas sensors, where such sensors can also be miniaturerized, wherein the there employed swellable polymer is applied at the surface of a thin membrane or bending structure within the silicon chip, wherein piezo resistors are entered as mechano-electrical transducer elements below the polymer in the silicon. Such a solution is again not useful for chemical sensors for liquids on the basis of polymeric networks, since the liquid interferes in contrast to humid air and gases in all up to now known cases with the piezo resistors long-term also through the usually employed passivation layer between polymer and silicon and in particular cause corrosion at the required contract locations, which connect resistors electrically to the outside. Furthermore the elasticity module is substantially smaller for the above recited polymer networks as compared to the elasticity module observed for the polymers with the bimorphous gas and humidity sensors, such that the tension caused by swelling in the polymeric network operates only as out-of-plane-component and therewith leads to too small a deflection of the membrane or, respectively, of the bending structure for practical applications.

These problems were resolved in the German printed Patent document DE 10129 985 C2, German printed Patent document DE 10129986 C2, and German printed Patent document DE 101 29 987 C2. However in connection with the use of electrolytical gels, for example for pH measurement, hysteresis effects and under certain application conditions also midterm irreversible changes in the gel can occur, which negatively influence the long-term behavior (G. Gerlach, M. Gunther, J. Sorber, G. Suchaneck, K.-F. Arndt, A. Richter: chemical and pH sensors based on the swelling behavior of hydro gels. Sensors and actuators B 111-112 (2005), 555-561). A cause for this can be sought in the shielding effect or, respectively, the screening effect (A. Suzuki, H. Suzuki: Hysteretic behavior and irreversibility of polymer gels by pH change. J. Chem. Phys. Vol 103 No 11 (1995), 4706-4710), wherein the ionized groups in higher pH ranges are shielded by an excess of sodium ions and weaken the osmotic pressure. The excess of sodium ions starting with a certain threshold can lead to long living defects in the swelled polymer network.

PRESENTATION OF THE INVENTION

Therefore, it is an object of the present Invention to furnish a chemical sensor and a method for measuring the concentration of chemical components in liquids on the basis of swellable polymer networks, which chemical sensor and method avoid the recited disadvantages and make it possible based on the principle of force compensation, to drastically minimize volume changes of the gel and thereby to drastically minimize further penetration of swelling agent, wherein the reaction time to property changes of the measurement liquid are clearly shortened, and wherein miniaturerizable sensors on a semiconductor basis are realized, and wherein as well as a strict separation is maintained of the interacting liquid from an evaluation electronics.

In accordance with the Invention the object is achieved by a sensor arrangement for measuring a concentration of a component in a liquid. A hollow chamber is formed in part by a deformation body, wherein the hollow chamber on a side is deformable through the deformation body and on other sides is rigidly delimited. The hollow chamber forms part of a base body (2). At least one opening is formed in at least one of the other rigid delimiting sides of the hollow chamber. A swellable polymer network is disposed in the hollow chamber. The swellable polymeric network exhibits a volume phase transition at a certain concentration of components in a liquid and the liquid can have contact with the polymeric network through the opening. A mechano electrical transducer interacts with the deformation body for detecting a deflection of the deformation body. A servo device (8) works on the deformation body (3). A comparator unit forms part of a control member. The servo device (8) is controllable through the control member such that a deflection of the deformation body (3) is compensated, and in that the corresponding control signal for the servo device (8) is the measurement size for the concentration of components in the liquid (1).

The base body (2) can a semiconductor chip (10), wherein the semiconductor chip (10) comprises a hollow chamber (6) and is mounted to a support (11). The deformation body (3) can be locally thinned out as a bending plate or as a membrane. The deformation body (3) can comprise one or several piezo resistive resistors (13) as mechano electrical transducers (4). The deformation body (3) can support the movable electrode of a capacitor arrangement, which movable electrode forms the mechano electrical transducer (4). The mechano electrical transducer (4) can be integrated into the servo device (8). The servo device (8) can be a piezo electric element or the servo device (8) can be an electrodynamic element. The servo device (8) can be formed of a temperature sensitive polymer network and a heating device. The polymeric network (5) can be located in the hollow chamber (6) and can exhibit also a temperature sensitivity in addition to the desired sensitivity relative to a component in the liquid and assumes itself the function of a servo device. The mechano electrical transducer (4) can be a measurement device coupled with the servo device (8). The polymeric network (5) can be applied as a thin layer in the hollow chamber (6) on the deformation body (3). The polymeric network (5) can be entered as a body in the hollow chamber (6) between the deformation body (3) and the support (11). The base body (2) can be a semiconductor chip (10), wherein the semiconductor chip (10) comprises a hollow chamber (6) and is mounted on a support (11), wherein the support has at least one feed flow (12a) and at least one discharge flow (12b) and wherein the liquid (1) has a continuous contact to the polymeric network (5) through the support (11). The base body (2) can be a semiconductor chip (10), wherein the semiconductor chip (10) comprises a hollow chamber (6) and is mounted on the support (11), wherein the support (11) is coupled to an open volume.

A method for measurement of the concentration of components in a liquid is further disclosed. A sensor exhibits a base body with a deformation body, and a hollow chamber. The hollow chamber on the one side is deformable through the deformation body and on the other side is rigidly closed. The hollow chamber is completely filled with a swellable polymeric network, which exhibits at a certain concentration of components in the liquid a volume phase transition. The liquid has contact to the polymeric network through at least one opening in at least one of the rigid limitation sides of the hollow chamber. A mechano electrical transducer detects the deflection of the deformation body. The servo device (8) works on the deformation body (3) and is controlled continuously through a control member with a comparator unit (9). The deflection of the deformation body (3) is continuously compensated, and wherein the respective control signal for the servo device (8) is employed as a measurement value for the concentration of components in the liquid (1).

ADVANTAGEOUS EFFECTS OF THE INVENTION

The Invention is based thereon that the deformation of a deformation body generated based on the functioning of a swellable polymeric network (hydro gel) is continuously observed by a comparator unit and compensated by a servo device. It is thereby accomplished that the servo device exerts a force, wherein the force corresponds precisely to the force exerted by the osmotic pressure in the polymer network, such that the polymer network remains nearly unchanged. The correcting variable, which is therefore the current in case of an electro dynamic immersion coil drive as a servo device, corresponds to the concentration of the chemical component in the measurement liquid.

Based on this arrangement according to the present Invention on the one hand a strict separation of electronics and liquid are accomplished as a precondition for a long-term stable sensor without influencing the electrical components and on the other hand shortened adjustment times of the sensor are to be expected based on the minimized penetration of the swelling agent.

The sensor according to the present Invention can exhibit a variety of forms and embodiments:

A thinned region of a semiconductor chip can form a deformable membrane as a deformation body and thereby itself operates as a mechano electrical transducer by containing piezo resistors, wherein the piezo resistors transform the deformation of the membrane into a change of the resistance of the piezo resistor and therewith into an electrical signal. A deformable thinned out region of a semiconductor chip can however also directly or indirectly be part of a changeable capacitor. Further mechano electrical transducer mechanisms, such as for example mechano optical, magneto optical and others are also possible with the sensor according to the present Invention. The deformation body can comprise also stainless-steel or a polymer. The servo device can be an immersion coil drive, a piezo drive, or, with limitations, also an electrochemical drive and therewith for example can comprise a polymer network and a heating device. According to a further embodiment, the mechano electrical transducer can be integrated into the servo device. The polymer network can both as a thin layer as well as also as a body be entered into the hollow chamber between the deformation body and the support. Furthermore the polymeric network, in addition to the desired sensitivity relative to components in the liquid, can additionally exhibit a sensitivity to temperature and therewith itself assume the function of a servo device.

BEST PATHS FOR PERFORMING THE INVENTION

Figure 2:
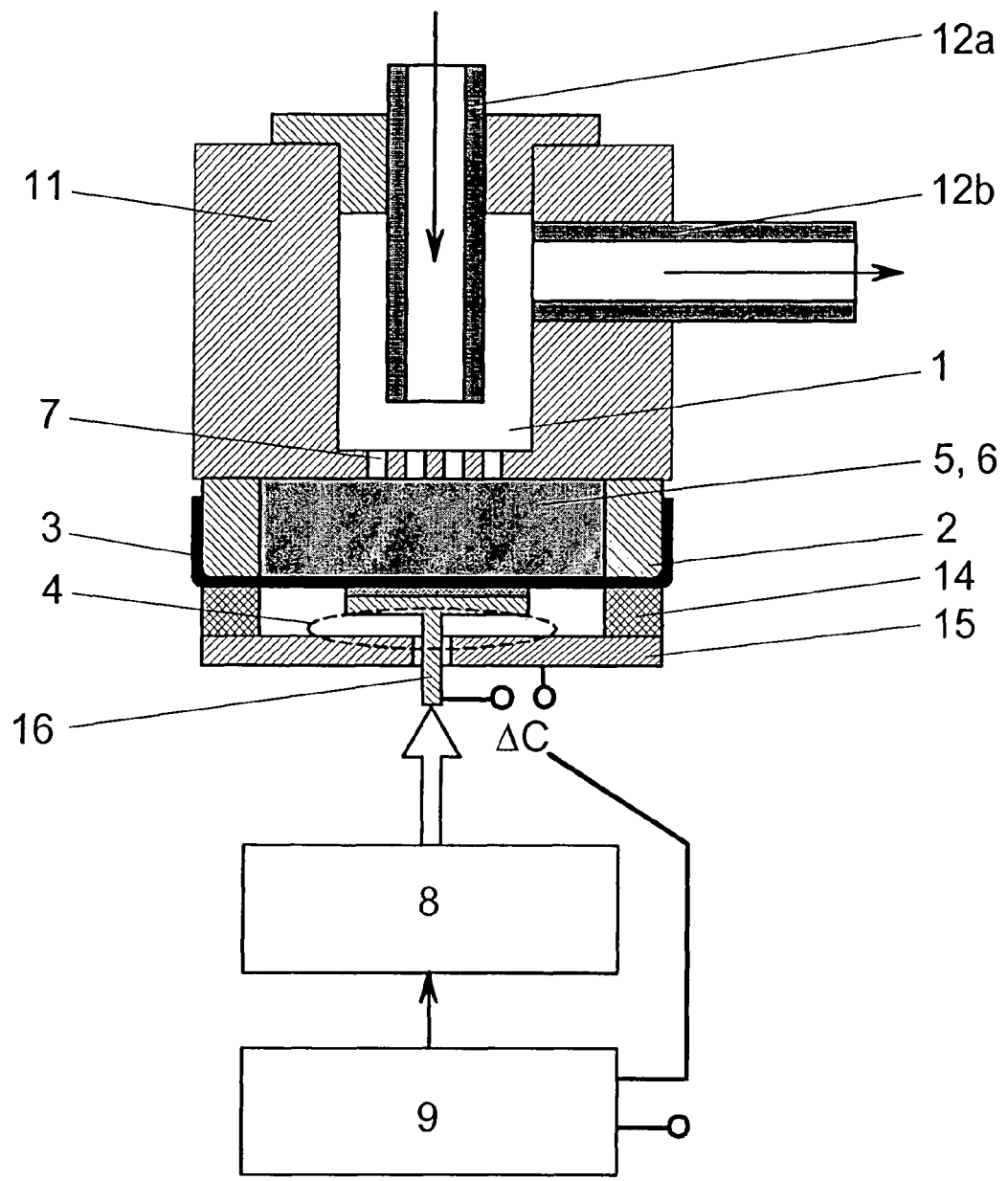

The invention is illustrated in more detail in the following by way of two advantageous embodiment examples. There is shown in the drawings:

FIG. 1 shows a first embodiment of a sensor according to the present Invention under using a semiconductor chip with the piezo resistive mechano electrical transformation for obtaining the feedback value for the comparator unit, and FIG. 2 shows the second embodiment of a sensor according to the present Invention with the deformation body made from stainless-steel, wherein the feedback value is captured as a capacitance change.

A FIG. 1 shows an embodiment of the sensor according to the present Invention for measuring the concentration of chemical components such as for example alcohol in liquids 1, wherein a swelling or de-swelling of a polymer network 5 capable of swelling, for example of the neutral hydro gel poly-N-iso-propyl-acryl-amide, would be caused by the chemical component in the liquid 1.

The polymeric network 5 is disposed in the hollow chamber 6, wherein the hollow chamber 6 is formed here by a semiconductor chip 10 with a thinned region as a deformation body 3, and a completely filled hollow chamber 6. The surface of the semiconductor chip 10 disposed opposite to the thinned out region forms or contains completely or partially a mechano electrical transducer 4, here furnished as one or several piezo resistors 13. The piezo resistors 13 and the liquid 1 to be measured are disposed therewith on opposite sides of a semiconductor chip 10 forming a base body 2 and are therefore strictly separated from each other. The sensor furthermore contains on this side of the liquid 1 a support 11, wherein the support 11 is here perforated with at least one opening 7 in order to enable on the one hand the access of the liquid 1 to the polymeric network 5 and on the other hand the retaining of the polymeric network 5 in the hollow chamber 6. However, the openings 7 are such small and mechanically stiff that, during swelling of the polymer network 5, the deformation body 3 is deflected and therewith the resistance change of the piezo resistor 13 is generated. The support 11 has a feed flow 12a and the discharge flow 12b through which the liquid 1 has continuous contact with the polymeric network 5. Alternatively, the support 11 is coupled to an open volume. The deflection of the deformation body 3 is captured by a control member of the comparator unit 9 with the aid of the resistance change of the piezo resistors 13 and is compensated by a suitable control of a servo device 8. The required control signal for the servo device represents the concentration of a selected chemical component in the liquid.

FIG. 2 shows an embodiment were in contrast to FIG. 1 the mechano electrical transducer 4 is formed by electrodes. One of the electrodes is a fixedly positioned disk 15, which serves as a fixed reference element of the capacitance evaluation through a distance spacer 14. A capacitance change is accomplished through a tappet transferring the restoring force from the servo device 8 through the deformation of the deforming body 3 caused by the swelled polymer network 5. This tappet 16 forms the second electrode. The deformation body 3 comprises here a stainless-steel foil. While using the poly electrolytical hydro gel poly-vinyl-alcohol/poly-acrylic-acid, a volume phase transition, for example by ion presence, in particular through the pH value, can be released.

It will be understood that each of the elements described above, or two or more together, may also find a useful application in other types of analytic testing system configurations and liquid measuring and analyzing procedures differing from the types described above.

While the invention has been illustrated and described as embodied in the context of a sensor and methods for measuring of concentrations of components in a liquid, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

A LIST OF REFERENCE CHARACTERS

1—liquid
2—base body
3—deformation body
4—mechano electrical transducer
5—swellable polymeric network (hydro gel)
6—hollow chamber
7—opening
8—servo device
9—comparator unit
10—semiconductor chip
11—support
12a—feed flow
12b—discharge flow
13—piezo resistive resistors
14—distance spacer
15—disk
16—tappet

The invention claimed is:

1. A sensor for measuring the concentration of a component in a liquid, exhibiting a base body with a deformation body, a hollow chamber, wherein the hollow chamber on the one side is deformable through the deformation body and on the other side is rigidly closed, wherein the hollow chamber is filled with a swellable polymeric network which exhibits a volume phase transition at a certain concentration of a component in the liquid and through at least one opening in at least one of the rigid delimiting sides of the hollow chamber the liquid can have contact with the swellable polymeric network and wherein a mechano electrical transducer detects the deflection of the deformation body,
characterized in that
the sensor exhibits a servo device (8) contacting, working and exercising a mechanical force on the deformation body (3), wherein the servo device (8) is thus controllable by a control signal of a control member with a comparator unit (9) such that the deflection of the deformation body (3) is compensated by a force of the servo device (8) exerted on the deformation body (3) corresponding to balancing a displacement force of the swellable polymeric network (5) acting on the deformation body (3), and in that the corresponding control signal for the servo device (8) is the measurement value for the concentration of a component in the liquid (1).

2. The sensor according to claim 1, wherein the base body (2) is a semiconductor chip (10), wherein the semiconductor chip (10) surrounds a hollow chamber (6) and is mounted to a support (11).

3. The sensor according to claim 1, wherein the deformation body (3) is locally thinned out as a bending plate or as a membrane.

4. The sensor according to claim 1, wherein the deformation body (3) faces and interacts with one or several piezo resistive resistors (13) operating as mechano electrical transducers (4).

5. The sensor according to claim 1, wherein the deformation body (3) supports a movable electrode of a capacitor arrangement, which movable electrode forms the mechano electrical transducer (4).

6. The sensor according to claim 1, wherein the mechano electrical transducer (4) is integrated into the servo device (8).

7. The sensor according to claim 1, wherein the servo device (8) is a piezo electric element.

8. The sensor according to claim 1, wherein the servo device (8) is an electrodynamic element.

9. A sensor for measuring the concentration of a component in a liquid, exhibiting a base body with a deformation body, a hollow chamber, wherein the hollow chamber on the one side is deformable through the deformation body and on the other side is rigidly closed, wherein the hollow chamber is completely filled with a swellable polymeric network which exhibits a volume phase transition at a certain concentration of a component in the liquid and through at least one opening in at least one of the rigid delimiting sides of the hollow chamber the liquid can have contact with the polymeric network and wherein a mechano electrical transducer detects the deflection of the deformation body,
characterized in that
the sensor exhibits a servo device (8) working on the deformation body (3), wherein the servo device (8) is thus controllable through a control member with a comparator unit (9) such that the deflection of the deformation body (3) is compensated, and in that the corresponding control signal for the servo device (8) is the measurement size for the concentration of components in the liquid (1), wherein the servo device (8) interacts with a temperature sensitive polymer network and a heating device.

10. The sensor according to claim 1, wherein the swellable polymeric network (5) is located in the hollow chamber (6) and exhibits also a temperature sensitivity in addition to a desired sensitivity relative to a component in the liquid and performs the function of being compressed by the servo device (8).

11. The sensor according to claim 1, wherein the mechano electrical transducer (4) is a measurement device coupled with the servo device (8).

12. The sensor according to claim 1, wherein the swellable polymeric network (5) is applied as a thin layer in the hollow chamber (6) on the deformation body (3).

13. The sensor according to claim 1, wherein the swellable polymeric network (5) is entered as a body in the hollow chamber (6) between the deformation body (3) and the support (11).

14. A sensor for measuring the concentration of a component in a liquid, exhibiting a base body with a deformation body, a hollow chamber, wherein the hollow chamber on the one side is deformable through the deformation body and on the other side is rigidly closed, wherein the hollow chamber is completely filled with the swellable polymeric network which exhibits a volume phase transition at a certain concentration of components in the liquid and through at least one opening in at least one of the rigid delimiting sides of the hollow chamber the liquid can have contact with the polymeric network and wherein a mechano electrical transducer detects the deflection of the deformation body,
characterized in that
the sensor exhibits a servo device (8) working on the deformation body (3), wherein the servo device (8) is thus controllable through a control member with a comparator unit (9) such that the deflection of the deformation body (3) is compensated, and in that the corresponding control signal for the servo device (8) is the measurement size for the concentration of components in the liquid (1), wherein the base body (2) is a semiconductor chip (10), wherein the semiconductor chip (10) comprises the hollow chamber (6) and is mounted on a support (11), wherein the support has at least one feed flow (12a) and at least one discharge flow (12b) and wherein the liquid (1) has a continuous contact to the polymeric network (5) through the support (11).

15. The sensor according to claim 1, wherein the base body (2) is a semiconductor chip (10), wherein the semiconductor chip (10) surrounds the hollow chamber (6) and is mounted on the support (11), wherein the hollow chamber (6) is coupled to an open volume through openings (7) in the support (11).

16. A sensor for measuring a concentration of a component in a liquid comprising
a base body (2);
a hollow rigid chamber (6) having one side open and delimited in part by the base body (2);
a swellable polymeric network (5) disposed in and rigidly contained in the hollow rigid chamber (6), wherein the swellable polymeric network (5) has a shiftable face located at the open side of the hollow rigid chamber (6), wherein the swellable polymeric network (5) exhibits a volume phase transition occurring at a certain concentration of a component in a liquid;
a deformation body (3) covering the open side of the hollow rigid chamber (6) and of the shiftable face of the swellable polymeric network (5) for following position changes of the shiftable face;
a signal detector (4, 15, 16) interacting with the deformation body (3) for detecting a displacement of the deformation body (3) at the open side of the hollow rigid chamber (6);
a comparator unit (9) connected to the signal detector (4, 15, 16) for receiving a detection signal of a displacement of the deformation body (3) and for generating a control signal;

a servo device (8) connected to the comparator unit (9) for receiving the control signal from the comparator unit (9) and engaging the deformation body (3) with a force for opposing a displacement of the deformation body (3) and for compensating the displacement of the deformation body (3) and wherein the control signal for the servo device (8) is a measurement value for a concentration of a component in the liquid (1).

17. The sensor according to claim 16 further comprising
a support (11) extending the base body (2) for forming a surrounding of the hollow rigid chamber (6), wherein the base body (2) is a semiconductor;
an opening (7) in the hollow rigid chamber (6) in addition to and outside of the open side of the hollow rigid chamber (6) for accessing the swellable polymeric network (5) such that the liquid (1) can have contact with the swellable polymeric network (5) through the opening (7) in the hollow rigid chamber (6);
a feed flow path (12*a*) connected to the opening (7) for feeding in a liquid (1);
a discharge flow path (12*b*) connected to the opening (7) for discharging the liquid (1); and wherein the liquid (1) has a continuous contact to the swellable polymeric network (5) through the opening (7);
wherein the signal detector (4, 15, 16) is a mechano electrical transducer (4).

18. The sensor according to claim 16 further comprising
a distance spacer (14) formed near an outer periphery of the deformation body (3) for defining a distance from the deformation body (3);
a fixedly positioned disk (15) attached to the distance spacer (14) and forming a first electrode and serving as a fixed reference element of a capacitance evaluation;
a tappet (16) transferring a restoring force from the servo device (8) through the deformation of the deformation body (3) caused by the swellable polymer network (5) and forming a second electrode for accomplishing a capacitance change; wherein the fixedly positioned disk (15) and the tappet (16) form the signal detector (4, 15, 16).

19. A method for measurement of the concentration of components in a liquid with a sensor comprising the steps:
connecting a comparator unit (9) to a servo device (8);
placing a deformation body (3) onto the servo device (8);
generating a control signal in the comparator unit (9);
delivering the control signal from the comparator unit (9) to the servo device (8) for controlling a force of the servo device (8) interacting with the deformation body (3);
placing a mechano electrical transducer (4) at the deformation body;
connecting the mechano electrical transducer (4) to the comparator unit (9);
delivering a detection signal of the displacement from the mechano electrical transducer (4) to the comparator unit (9);
detecting a displacement of the deformation body (3) with the mechano electrical transducer (4);
compensating the displacement of the deformation body (3);
disposing a swellable polymeric network (5) at the deformation body (3);
shifting the deformation body (3) with the liquid having the component and contacting the swellable polymeric network (5);
surrounding the swellable polymeric network (5) with a hollow rigid chamber (6) having an open side for positioning the deformation body (3), wherein the hollow rigid chamber (6) is filled with the swellable polymeric network (5), which exhibits a volume phase transition at a certain concentration of a component in the liquid (1);
providing an opening (7) in the hollow rigid chamber (6), wherein the liquid has contact to the swellable polymeric network through the opening (7) in the hollow chamber (6);
feeding a liquid with a component to the opening;
employing the control signal for the servo device (8) as a measurement value for a concentration of a component in the liquid (1).

\* \* \* \* \*